United States Patent [19]

Kossoff et al.

[11] 4,455,872

[45] Jun. 26, 1984

[54] ROTATING ULTRASONIC SCANNER

[75] Inventors: George Kossoff, Northbridge; Jack Jellins, Rose Bay, both of Australia

[73] Assignee: Commonwealth of Australia, The Department of Health, Phillip, Australia

[21] Appl. No.: 480,830

[22] Filed: Apr. 25, 1983

Related U.S. Application Data

[63] Continuation of Ser. No. 193,974, Oct. 6, 1980, abandoned, which is a continuation of Ser. No. 16,513, Mar. 1, 1979, abandoned.

[30] Foreign Application Priority Data

Mar. 3, 1978 [AU] Australia .............................. PD3579

[51] Int. Cl.³ .............................................. G01N 29/04
[52] U.S. Cl. ...................................... 73/618; 73/621; 73/633; 128/660

[58] Field of Search ................. 73/633, 634, 618, 621, 73/620; 128/660

[56] References Cited

U.S. PATENT DOCUMENTS 3,885,437  5/1975  Reagan ......................... 73/421.5 A

FOREIGN PATENT DOCUMENTS 1600873   9/1970  France .................................. 73/633
1046774  10/1966  United Kingdom ................ 73/620

Primary Examiner—Anthony V. Ciarlante

[57] ABSTRACT

A rotating scanner for use in ultrasonic echoscopy has a linearly scanned transducer arrangement, for transmitting beams of ultrasonic energy into an object (and receiving reflected ultrasonic echoes from the object). The transducer arrangement is rotated about an axis passing through the center or one end of the linear scan. The linear scanning may be mechanical scanning, or by electronic switching of an array of transducer elements.

10 Claims, 4 Drawing Figures

ROTATING ULTRASONIC SCANNER

This is a continuation of application Ser. No. 193,974, filed Oct. 6, 1980, now abandoned, which is a continuation of application Ser. No. 16,513, filed Mar. 1, 1979, now abandoned.

FIELD OF THE INVENTION

This invention relates to the technique of ultrasonic echoscopy of objects and in particular to apparatus whereby a more complete and useful examination of the object may be effected. It is particularly, but not solely, directed to the use of echoscopy in medical diagnostic examination.

BACKGROUND TO THE INVENTION

Ultrasonic echoscopy provides information about an examined object which may be displayed in the form of an ultrasonic echogram. Such an echogram consists of a display of acoustic impedance discontinuities or reflecting surfaces in the object. It is obtained by directing a short pulse of ultrasonic energy, typically in the 1–30 MHz frequency range, into the examined object where any acoustic impedance discontinuities in the object reflect and return some of the energy in the form of an echo. This echo is received, converted into an electric signal and displayed as an echogram on a cathode ray oscilloscope, a film, a chart or the like.

The echogram may constitute either a one dimensional or a two dimensional representation and in both cases the information is contained in the position and magnitude of the echo displayed. In a one dimensional display, the position along a base line is used to indicate the distance to the reflecting surface whilst the magnitude of the echo is displayed for example as a deflection of the base line "A mode" or as an intensity change "B mode". In a two dimensional display, the position along a base line is used to indicate the distance to the reflecting surface as in a one dimensional display, and the direction of the base line is used to represent the direction of propagation of the acoustic energy. The two dimensional display is obtained by changing this direction of propagation of the acoustic energy and by instituting a similar but not necessarily identical movement of the base line of the display. The magnitude of the echo is displayed as for a one dimensional display, for example, as a deflection of the base line or as an intensity change.

The technique of ultrasonic echoscopy is used in medical diagnosis to obtain information about the anatomy of patients. This application of echoscopy is now well known. It has been described, for example, by D. E. Robinson in Proceedings of the Institution of Radio and Electronics Engineers Australia, Vol. 31, No. 11, pages 385–392, Nov. 1970, in his paper entitled "The Application of Ultrasound in Medical Diagnosis". As pointed out in that article, ultrasonic echoscopy may be used to produce displays resembling anatomical cross-sections which have proved clinically useful when the desired information concerns physical dimensions, shapes of organs or structures or the like. Ultrasonic echography has proved of particular value as a diagnostic aid in the abdomen and pregnant uterus, eye, breast, brain, lung, kidney, liver and heart, these being areas of soft tissue with little bone and air.

In general, ultrasonic echoscopy is considered to complement other techniques to provide a more complete picture of the patient's condition. However, particularly in pregnancies, ultrasonic echoscopy may be useful in place of X-rays where the latter may not give sufficient information or may be dangerous.

In medical use, a pulse of ultrasonic energy is transmitted into a patient in a known direction and echoes are received from reflecting surfaces within the body. The time delay between a transmitted pulse and the received echo depends on the distance from the transmitter to the reflecting surface and the distance information so obtained may be displayed in a suitable way for interpretation and clinical use as a one-dimensional range reading or as a two-dimensional cross-section as previously described.

In many ultrasonic B mode investigations it is an advantage to scan quickly over the desired area. Quick scanning may be achieved either by mechanical means such as by linearly translating the transducer over the desired length or by oscillating the transducer over the desired angle, the speed of movement being determined by considerations such as the desired line density of the ultrasonic information. Alternatively linear and oscillatory scanning may be achieved by electronic means such as may be obtained with a switched linear array transducer or a sectoring phased array transducer.

DISCLOSURE OF THE PRESENT INVENTION

It is an object of the present invention to provide an improved means for and method of scanning an area of an object under examination by ultrasonic echoscopy.

In accordance with one aspect of this invention, apparatus for use in ultrasonic echoscopic examination of an object comprises:

(a) a transducer for transmitting beams of ultrasonic energy into said object in a predetermined direction relative to said transducer;

(b) means for linearly scanning said beams; and (c) means for sweeping said linearly scanned beams about an axis passing through the center or one end of said linear scan.

Thus, using the present invention, it is possible to perform ultrasonic examination of an object utilizing a single transducer which is either translated or oscillated in a plane to provide a cross sectional image in that plane. Alternatively, a linear array of transducer elements may be activated to provide a cross-sectional. With either form of apparatus, the scanned image of the object in the said plane is rotated during the examination of the object so as to sequentially generate a series of sections. Thus, the rotational movement of the scanning plane of the transducer arrangement is effective to achieve the visualisation over a volume within the object under examination.

The rotation of the transducer can conveniently be achieved by mechanical means. Alternatively, a two-dimensional multi-element transducer may be employed, in which case the rotation can be effected, by electrical or electronic switching. The centre of rotation can be at the center of the scanning plan (thus giving a series of diametric sections), at the edge of the scanning plane (giving a series of radial sections), outside the scanning plane (so as to permit the examination of an annular volume), or at any required location within the scanning plane. The present invention is particularly useful in ultrasonic echoscopy where it is necessary to scan a volume having substantially circular symmetry—such as the female breast.

Where a single transducer is used in the present invention, it may be of the fixed focus or annular array focused type. In use, the present invention may be adapted for the examination of an object with either the contact method (using direct or through-a-membrane contact between the transducer with the object), or with the water coupling method in which the transducer is immersed in a water tank. The transducer may be positioned as desired to provide horizontal, vertical or any other inclined cross-sectional images of the object.

The examination technique in accordance with the present invention is particularly appropriate when only a few landmarks are available to identify the examined area. For instance, in the ultrasonic examination of the breast, the nipple provides the only accurate anatomical landmark. Thus a series of scanned diametrical or radial sections through the breast with the nipple at the centre or at the edge of the scan will provide an ultrasonic examination of the whole organ. Because the nipple is portrayed in every scan, accurate localisation of all visualised detail is obtainable.

In cases where the scanning technique employed is such as to provide simple scanning of the object only, the scanning may also embody a tilting motion of the plane of the scan tilting can be used, for example, to change the direction of enhancement and shadowing that is obtained from localised areas of tissues with different attenuation or to examine different posterier tissues. The present invention may also be used in compound ultrasonic scanning of an object.

DETAILED DESCRIPTION OF ILLUSTRATED EMBODIMENT

Figure 1:
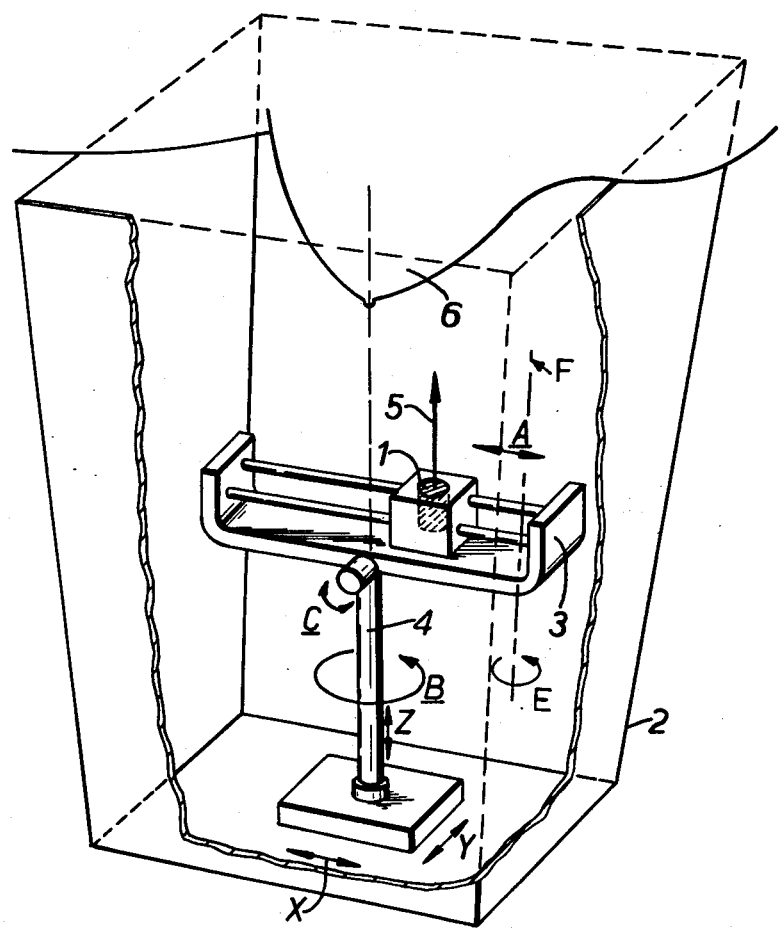
FIG. 1 is a perspective view of a mechanically scanned, mechanically rotated, embodiment of the present invention, positioned within a water tank, and used to scan the female breast.

In the embodiment illustrated in FIG. 1, an ultrasonic transducer 1 is contained in a water tank 2 and is directed upwardly therein so as to transmit pulses of ultrasonic energy along the beam axis 5. Means are provided to mechanically translate the transducer 1 reciprocally in the direction shown by the double arrow A, at a relatively quick rate of (for example) one fifth of a second for a traverse along the length of the carriage 3, which defines the cross-sectional plane of the image. By way of example, a reciprocating linear scanner of the type disclosed in Australian Patent Specification No. 35579/78 may be used to mechanically translate the transducer 1.

Means are provided to rotate the carriage 3 as shown by arrow B underneath the breast 6 to be examined, the breast being immersed in the water contained in tank 2. The speed of rotation of the carriage 3 is typically of the order of 180° per minute, although this may be varied as determined by factors such as the requirement to provide cross-sectional visualisations of the object that have a certain angular control. Rotation of the carriage 3 may be achieved by use of an electric motor geared to or in other suitable driving relationship with the carriage 3.

Preferably, means are provided within the tank 2 to move the transducer and carriage assembly in the directions of the arrows "X" and "Y" so that the center of rotation of the carriage can be positioned as desired, for example, at the nipple of breast 6. Suitable means may also be provided to adjust the transducer and carriage assembly in the direction of the arrow "Z" to position the transducer at the required distance from the breast. Furthermore, carriage 3 may be pivotally mounted on the supporting structure 4 and suitable means are provided to tilt the carriage 3 as shown by the arrow C. The supporting structure 4 may be alternatively attached at or near an end of carriage 3 coincident with axis F, causing the carriage to rotate as depicted at E. U.S. Pat. No. 4,094,306 discloses a suitable supporting mechanism whereby tilting and movement in the "X", "Y" and "Z" directions with respect to the object may be effected.

Figure 2A:
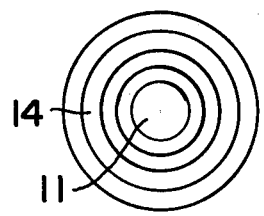
FIG. 2 illustrates, schematically, four well known different constructions of ultrasonic transducer arrays.

Modifications of this form of apparatus are, of course, possible. For example, as foreshadowed earlier in this specification, the single element transducer 1 may be replaced by an annular array transducer as shown in FIG. 2(a). This form of transducer comprises a central disc 11 and a number of separate co-axial annuli, of which element 14 is a typical example. By introducing delays in the reception of the ultrasonic signals by these elements, dynamic focussing of the ultrasonic beam can be achieved.

Dynamic focussing, as is well known in the field of echoscopy, provides optimal resolution along the line of sight. An advantage of the use of this type of transducer in the apparatus of FIG. 1 is that the means to adjust the carriage assembly in the "Z" direction is unnecessary.

Figure 2B:
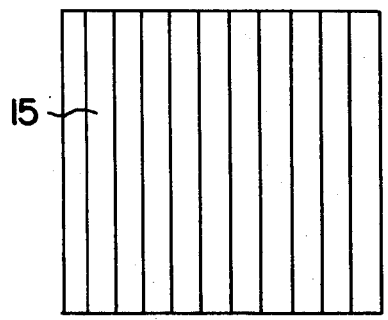

As also foreshadowed earlier in this description, the reciprocating linear scanner component of the apparatus illustrated in FIG. 1 will be unnecessary if, instead of a single focus transducer 1 or the annular array structure of FIG. 2(a), a transducer having a linear array structure as illustrated in FIG. 2(b) is used. Linear array transducers, which are also well-known in echoscopy, comprise a large number of narrow rectangular elements such as the typical element 15 of FIG. 2(b). These elements are arranged in a row and are electrically sequenced to produce either sector or linear scans. Focussing may also be introduced on the reception phase.

Figure 2C:
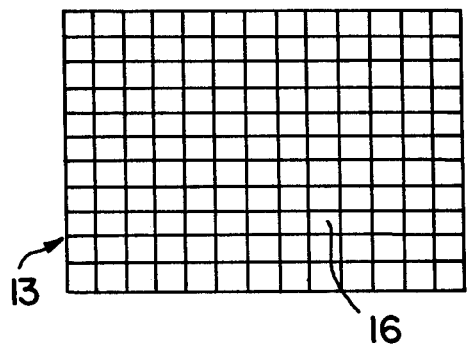

Another form of the present invention was also foreshadowed earlier in this description, namely the use of a two-dimensional multi-element transducer and electronic switching to effect the scanning of the method of the present invention. The type of transducer used for such electronic scanning is, as will be appreciated by those skilled in this art, a transducer of the type illustrated in FIG. 2(c). As shown in this figure, the two-dimensional array structure 13 comprises a large number of individual transducer elements, such as the typical element 16. These elements are arranged in rows and columns and scanning planes may be obtained at an angle across the structure, and in any desired direction, by appropriate electrical sequencing.

While the present invention has been described with reference to one particular embodiment, it will be generally understood by those skilled in the art that various changes may be made and equivalents may be substituted for elements thereof without departing from the true spirit and scope of the invention.

We claim:

1. Apparatus for obtaining a series of sectional ultrasonic scans of an object, said scans extending radially from a substantially central reference point on the object and being angularly displaced relative to each other, said apparatus comprising:

(a) a transducer for transmitting pulses of ultrasonic energy into said object in a predetermined direction relative to said transducer and for receiving echoes of said pulses of energy that are reflected by acoustic impedance discontinuities within said object;

(b) means for changing the spatial location of the pulses of ultrasonic energy along a linear path relative to said reference point, to thereby establish a plurality of beams along which said pulses are transmitted; and (c) means for sweeping said linear path about an axis passing through the central reference point and center or one end of said linear scan, at a rate which is substantially slower than the rate of changing the spatial location of said pulses along the linear path.

2. Apparatus as defined in claim 1, in which said transducer transmits beams in a fixed direction and is mounted on a carriage for reciprocal linear movement therealong to effect the changing spatial location of said pulses along the linear path, and said means for sweeping comprises means for rotating said carriage.

3. Apparatus according to claim 2, wherein said transducer is a fixed focused transducer.

4. Apparatus according to claim 2, wherein said transducer is an annular array focused transducer.

5. Apparatus according to claim 1, further comprising a housing adapted to be filled with a liquid coupling medium, said transducer being contained within said housing.

6. Apparatus according to claim 5, wherein said housing has a substantially horizontal upper surface, an aperture in said surface, and a flexible coupling membrane covering said aperture in a liquid-tight seal.

7. Apparatus as defined in claim 1, including means for tilting said carriage.

8. Apparatus as defined in claim 1, which said transducer is a linear array transducer which generates linearly scanned beams of ultrasonic energy by electronic switching, and said means for sweeping comprises means for mechanically rotating said linear array transducer.

9. Apparatus as defined in claim 1, in which said transducer comprises a two-dimensional array of transducer elements which generate linearly scanned beams of ultrasonic energy by electronic switching and said means for sweeping comprises additional electronic switching means associated with said transducer.

10. A method of obtaining a series of sectional ultrasonic scans of an object, said scans extending radially from a substantially central reference point on the object and being angularly displaced relative to each other, said method comprising the steps of:

(a) directing beams of ultrasonic energy into said object and receiving echoes of said ultrasonic energy from acoustic impedance discontinuities in said object;

(b) changing the spatial location of said beams along a linear path; and (c) rotating said linear path about an axis passing through the central reference point and the center of the path or at one end of the path at a rate which is substantially slower than the rate of changing the spatial location of said beams along the linear path.

* * * * *